United States Patent [19]
Stashenko et al.

[11] Patent Number: 5,624,801
[45] Date of Patent: Apr. 29, 1997

[54] METHODS OF IDENTIFYING HUMAN OSTEOCLAST-SPECIFIC AND RELATED GENES

[75] Inventors: Philip Stashenko, Norfolk; Yi-Ping Li, Boston; Anne L. Wucherpfennig, Brookline, all of Mass.

[73] Assignee: Forsyth Dental Infirmary for Children, Boston, Mass.

[21] Appl. No.: 457,304

[22] Filed: Jun. 1, 1995

Related U.S. Application Data

[62] Division of Ser. No. 392,678, Feb. 23, 1995, which is a continuation of Ser. No. 45,270, Apr. 6, 1993, abandoned.

[51] Int. Cl.$^6$ .................. C07H 21/02; C07H 21/04; C12Q 1/68
[52] U.S. Cl. .................. 435/6; 435/252.3; 435/370.1; 536/23.1
[58] Field of Search .................. 435/6, 320.1, 252.3; 536/23.1; 935/77, 78

[56] References Cited

PUBLICATIONS

Blair, Harry C., et al., "Extracellular-matrix degradation at acid pH Avian Osteoclast acid collagenase isolation and characterization," *Biochemical Journal* 290(3):873–884 (15 Mar. 1993).

Tezuka, Ken–Ichi, et al., "Identification of osteopontin in isolated rabbit osteoclasts," *Biochemical and Biophysical Research Communications* 186(2):911–917 (31 Jul. 1992).

Tezuka, Ken–Ichi, et al., "Molecular cloning of a possible cysteine proteinase predominantly expressed in osteoclasts'," *Journal of Biological Chemistry*, 269(2): 1106–1109, (14 Jan. 1994).

Horton, M.A. et al., "Monoclonal Antibodies ot Osteoclastomas (Giant Cell Bone Tumors): Definition ot Osteoclast–specific cellular Antigens," *Cancer Research*, 45:5663–5669 (Nov. 1985).

Davies, J. et al., "The Osteoclast Functional Antigen, Implicated in the Regulation of Bone Resoption, Is Biochemically Related to the Vitronectin Receptor," *The J. of Cell Biology*, 109:1817–1826 (Oct. 1989).

Hayman, A.R. et al., "Purification and Characterization of a Tartrate–resistant Acid Phosphatase form Human Osteoclastomas," *Biochem. J.*, 261:601–609 (1989).

Sandberg, M. et al., "Localization of the Expression of Types I, III, and IV Collagen, TFG–$\beta$1 and c–fos Genes in Developing Human Calvarial Bones," *Developmental Biology*, 130:324–334 (1988).

Sandberg, M. et al., "Enhanced Expression of the TGF–$\beta$ and c–fos mRNAs in the growth Plates of Developing Human Long Bones," *Development*, 102:461–470 (1988).

Ek–Rylander, B. et al., "Cloning, Sequence, and Developmental Expression of a Type 5, Tartrate–Resistant, Acid Phosphatase of Rat Bone," *The J. Biological Chem.*, 266:24684–24689 (Dec. 25, 1991).

Ek–Rylander et al., J. Biol. Chem. 266(36): 24684–24689, 1991.

Tezuka et al., Biochem. Biophys. Reseach Comm. 186(2) 911–917, 1992.

*Primary Examiner*—Stephanie Zitomer
*Assistant Examiner*—Paul B. Tran
*Attorney, Agent, or Firm*—Hamilton, Brook, Smith & Reynolds, P.C.

[57] ABSTRACT

The present invention relates to a method of identifying DNA encoding an osteoclast-specific or -related gene product. The method comprises hybridizing DNA with a stromal cell+, osteoclast+probe, or with cDNA or mRNA from an osteoclastoma, and with a stromal cell+, osteoclast–probe, or with cDNA or mRNA from stromal cells; and identifying DNA which hybridizes to the stromal cell+, osteoclast+ probe, or to cDNA or mRNA from osteoclastoma, but not to the stromal cell+, osteoclast–probe, or to cDNA or mRNA from stromal cells.

3 Claims, 1 Drawing Sheet

```
   1 AGACACCTCT GCCCTCACCA TGAGCCTCTG CCAGCCCCTG GTCCTGGTGC TCCTGGTGCT
  61 CGGCTGCTGC TTTGCTGCCC CCAGACAGCG CCAGTCCACC CTTGTGCTCT TCCCTGGAGA
 121 CCTGAGAACC AATCTCACCG ACAGGCAGCT GGCAGAGGAA TACCTGTACC GCTATCGTTA
 181 CACTCGGGTG GCAGAGATGC GTGGAGAGTC GAAATCTCTG GGGCCTGCCC TGCTGCTTCT
 241 CCAGAAGCAA CTGTCCCTGC CCGAGACCGG TGAGCTGGAT AGCGCCACGC TGAAGGCCAT
 301 GCGAACCCCA CGGTGCGGGG TCCCAGACCT GGGCAGATTC CAAACCTTTG AGGGCGACCT
 361 CAAGTGCCAC CACCACAACA TCACCTATTG GATCCAAAAC TACTCGGAAG ACTTGCCGCG
 421 GGCCGTGATT GACGACGCCT TTGCCCGCGC CTTCGCACTG TGGAGCGCGG TGACGCCGCT
 481 CACCTTCACT CGCGTGTACA GCCGGGACGC AGACATCGTC ATCCAGTTTG GTGTCGCGGA
 541 GCACGGAGAC CGGTATCCCT TCGACGGGAA GGACGGCTC CTGGCACACG CCTTTCCTCC
 601 TGGCCCCGCC ATTCAGGGAG ACGCCCATTT CGACGATGAC GAGTTGTGGT CCCTGGGCAA
 661 GGGCGTCGTG GTTCCAACTC GGTTTGGAAA CGCAGATGGC GCGGCCTGCC AGTTCCCCTT
 721 CATCTTCGAG GGCCGCTCCT ACTCTGCCTG CACCACCGAC GGTCGCTCCG ACGGCTTGCC
 781 CTGGTGCAGT ACCACGGCCA ACTACGACAC CGACGACCGG TTTGGCTTCT GCCCCAGCGA
 841 GAGACTCTAC ACCCGGGACG GCAATGCTGA TGGGAAACCC TGCCAGTTTC CATTCATCTT
 901 CCAAGGCCAA TCCTACTCCG CCTGCACCAC GGACGGTCGC TCCGACGGCT ACCGCTGGTG
 961 CGCCACCACC GCCAACTACG ACGGGACAA GCTCTTCGGC TTCTGCCCGA CCCGAGCTGA
1021 CTCGACGGTG ATGGGGGGCA ACTCGGCGGG GGAGCTGTGC GTCTTCCCCT TCACTTTCCT
1081 GGGTAAGGAG TACTCGACCT GTACCAGCGA GGGCCGCGGA GATGGGCGCC TCTGGTGCGC
1141 TACCACCTCG AACTTTGACA GCGACAAGAA GTGGGGCTTC TGCCCCGACC AAGGATACAG
1201 TTTGTTCCTC GTGGCGGCGC ATGAGTTCGG CCACGCGCTG GCTTAGATC ATTCCTCAGT
1261 GCCCGGAGGCG CTCATGTACC CTATGTACCG CTTCACTGAG GGCCCCCCT TGCATAAGGA
1321 CGACGTGAAT GGCATCCGGC ACCTCTATGG TCCTCCCCCT GAACCTGAGC CACGGCCTCC
1381 AACCACCACC ACACCGCAGC CCACGGCTCC CCCGACGGTC TGCCCCACCG GACCCCCAC
1441 TGTCCACCCC TCAGAGCGCC CCACAGCTGG CCCCACAGGT CCCCCCTCAG CTGGCCCCAC
1501 AGGTCCCCCC ACTGCTGGCC CTTCTACGGC CACTACTGTG CCTTTGAGTC CGGTGGACGA
1561 TGCCTGCAAC GTGAACATCT TCGACGCCAT CGCGGAGATT GGGAACCAGC TGTATTTGTT
1621 CAAGGATGGG AAGTACTGGC GATTCTCTGA GGGCAGGGCG AGCCGGCCGC AGGGCCCCTT
1681 CCTTATCGCC GACAAGTGGC CCGCGCTGCC CCGCAAGCTG GACTCGGTCT TGAGGAGCC
1741 GCTCTCCAAG AAGCTTTTCT TCTTCTCTGG GCCCCAGGTC TGGGTGTACA CAGGCGCGTC
1801 GGTGCTCGGC CCGAGCCGTC TGGACAAGCT GGGCCTGGA GCCGACGTGG CCCAGGTGAC
1861 CGGGCCCCTC CGGAGTGGCA GGGGAAGAT GCTGCTGTTC AGCGGGCGGC GCCTCTGGAG
1921 GTTCGACGTG AAGGCGCAGA TGGTGGATCC CCGGAGCGCC AGCGAGGTGG ACGGATGTT
1981 CCCCGGGGTG CCTTTGGACA CGCACGACGT CTTCCAGTAC CGAGAGAAAG CCTATTTCTG
2041 CCAGGACCGC TTCTACTGGC GCGTGAGTTC CCGGAGTGAG TTGAACCAGG TGGACCAAGT
2101 GGGCTACGTG ACCTATGACA TCCTGCAGTG CCCTGAGGAC TAGGGCTCCC GTCCTGCTTT
2161 GCAGTGCCAT GTAAATCCCC ACTGGGACCA ACCCTGGGA AGGAGCCAGT TTGCCGGATA
2221 CAAACTGGTA TTCTGTTCTG GAGGAAAGCG AGGAGTGGAG GTGGGCTGGG CCCTCTCTTC
2281 TCACCTTTGT TTTTTGTTGG AGTGTTTCTA ATAAACTTGG ATTCTCTAAC CTTT
```

METHODS OF IDENTIFYING HUMAN OSTEOCLAST-SPECIFIC AND RELATED GENES

This application is a division of co-pending application Ser. No. 08/392,678 filed Feb. 23, 1995, which is a file wrapper continuation of Ser. No. 08/045,270 filed Apr. 6, 1996, now abandoned.

BACKGROUND OF THE INVENTION

Excessive bone resorption by osteoclasts contributes to the pathology of many human diseases including arthritis, osteoporosis, periodontitis, and hypercalcemia of malignancy. During resorption, osteoclasts remove both the mineral and organic components of bone (Blair, H. C., et al., *J. Cell Biol.* 102:1164 (1986)). The mineral phase is solubilized by acidification of the sub-osteoclastic lacuna, thus allowing dissolution of hydroxyapatite (Vaes, G., *Clin. Orthop. Relat.* 231:239 (1988)). However, the mechanism(s) by which type I collagen, the major structural protein of bone, is degraded remains controversial. In addition, the regulation of osteoclastic activity is only partly understood. The lack of information concerning osteoclast function is due in part to the fact that these cells are extremely difficult to isolate as pure populations in large numbers. Furthermore, there are no osteoclastic cell lines available. An approach to studying osteoclast function that permits the identification of heretofore unknown osteoclast-specific or -related genes and gene products would allow identification of genes and gene products that are involved in the resorption of bone and in the regulation of osteoclastic activity. Therefore, identification of osteclast-specific or -related genes or gene products would prove useful in developing therapeutic strategies for the treatment of disorders involving aberrant bone resorption.

SUMMARY OF THE INVENTION

The present invention relates to isolated DNA sequences encoding all or a portion of osteoclast-specific or -related gene products. The present invention further relates to DNA constructs capable of replicating DNA encoding osteoclast-specific or -related gene products. In another embodiment, the invention relates to a DNA construct capable of directing expression of all or a portion of the osteoclast-specific or -related gene product in a host cell.

Also encompassed by the present invention are prokaryotic or eukaryotic cells transformed or transfected with a DNA construct encoding all or a portion of an osteoclast-specific or -related gene product. According to a particular embodiment, these cells are capable of replicating the DNA construct comprising the DNA encoding the osteoclast-specific or -related gene product, and, optionally, are capable of expressing the osteoclast-specific or -related gene product. Also claimed are antibodies raised against osteoclast-specific or -related gene products, or portions of these gene products.

The present invention further embraces a method of identifying osteoclast-specific or -related DNA sequences and DNA sequences identified in this manner. In one embodiment, cDNA encoding osteoclast is identified as follows: First, human giant cell tumor of the bone was used to 1) construct a cDNA library; 2) produce $^{32}$P-labelled cDNA to use as a stromal cell$^+$, osteoclast$^{30}$ probe, and 3) produce (by culturing) a stromal cell population lacking osteoclasts. The presence of osteoclasts in the giant cell tumor was confirmed by histological staining for the osteo-

2 clast marker, type 5 tartrate-resistant acid phosphatase (TRAP) and with the use of monoclonal antibody reagents.

The stromal cell population lacking osteoclasts was produced by dissociating cells of a giant cell tumor, then growing and passaging the cells in tissue culture until the cell population was homogeneous and appeared fibroblastic. The cultured stromal cell population did not contain osteoclasts. The cultured stromal cells were then used to produce a stromal cell$^+$, osteoclast$^{-32}$P-labelled cDNA probe.

The cDNA library produced from the giant cell tumor of the bone was then screened in duplicate for hybridization to the cDNA probes: one screen was performed with the giant cell tumor cDNA probe (stromal cell$^+$, osteoclast$^+$), while a duplicate screen was performed using the cultured stromal cell cDNA probe (stromal cell$^+$osteoclast$^-$) Hybridization to a stromal$^+$, osteoclast$^-$ probe, accompanied by failure to hybridize to a stromal$^+$, osteoclast$^{31}$ probe indicated that a clone contained nucleic acid sequences specifically expressed by osteoclasts.

In another embodiment, genomic DNA encoding osteoclast -specific or -related gene products is identified through known hybridization techniques or amplification techniques. In one embodiment, the present invention relates to a method of identifying DNA encoding an osteoclast-specific or -related protein, or gene product, by screening a cDNA library or a genomic DNA library with a DNA probe comprising one or more sequences selected from the group consisting of the DNA sequences set out in Table I (SEQ ID NOs: 1-32). Finally, the present invention relates to an osteoclast-specific or -related protein encoded by a nucleotide sequence comprising a DNA sequence selected from the group consisting of the sequences set out in Table I, or their complementary strands.

BRIEF DESCRIPTION OF THE FIGURE

The Figure shows the cDNA sequence (SEQ ID NO: 33) of human gelatinase B, and highlights those portions of the sequence represented by the osteoclast-specific or -related cDNA clones of the present invention.

DETAILED DESCRIPTION OF THE INVENTION

As described herein, Applicant has identified osteoclast-specific or osteoclast-related nucleic acid sequences. These sequences were identified as follows: Human giant cell tumor of the bone was used to 1) construct a cDNA library; 2) produce $^{32}$P-labelled cDNA to use as a stromal cell$^+$, osteoclast$^+$ probe, and 3) produce (by culturing) a stromal cell population lacking osteoclasts. The presence of osteoclasts in the giant cell tumor was confirmed by histological staining for the osteoclast marker, type 5 acid phosphatase (TRAP). In addition, monoclonal antibody reagents were used to characterize the multinucleated cells in the giant cell tumor, which cells were found to have a phenotype distinct from macrophages and consistent with osteoclasts.

The stromal cell population lacking osteoclasts was produced by dissociating cells of a giant cell tumor, then growing the cells in tissue culture for at least five passages. After five passages the cultured cell population was homogeneous and appeared fibroblastic. The cultured population contained no multinucleated cells at this point, tested negative for type 5 acid phosphatase, and tested variably alkaline phosphatase positive. That is, the cultured stromal cell population did not contain osteoclasts. The cultured stromal cells were then used to produce a stromal cell$^+$, osteoclast$^-$ 32P-labelled cDNA probe.

The cDNA library produced from the giant cell tumor of the bone was then screened in duplicate for hybridization to the cDNA probes: one screen was performed with the giant cell tumor cDNA probe (stromal cell⁺, osteoclast⁺), while a duplicate screen was performed using the cultured stromal cell cDNA probe (stromal cell⁺, osteoclast⁻). Clones that hybridized to the giant cell tumor cDNA probe (stromal⁺, osteoclast⁺), but not to the stromal cell cDNA probe (stromal⁺, osteoclast⁻), were assumed to contain nucleic acid sequences specifically expressed by osteoclasts.

As a result of the differential screen described herein, DNA specifically expressed in osteoclast cells characterized as described herein was identified. This DNA, and equivalent DNA sequences, is referred to herein as osteoclast-specific or osteoclast-related DNA. Osteoclast-specific or -related DNA of the present invention can be obtained from sources in which it occurs in nature, can be produced recombinantly or synthesized chemically; it can be cDNA, genomic DNA, recombinantly-produced DNA or chemically-produced DNA. An equivalent DNA sequence is one which hybridizes, under standard hybridization conditions, to an osteoclast-specific or -related DNA identified as described herein or to a complement thereof.

Differential screening of a human osteoclastoma cDNA library was performed to identify genes specifically expressed in osteoclasts. Of 12,000 clones screened, 195 clones were identified which are either uniquely expressed in osteoclasts, or are osteoclast-related. These clones were further identified as osteoclast-specific, as evidenced by failure to hybridize to mRNA derived from a variety of unrelated human cell types, including epithelium, fibroblasts, lymphocytes, myelomonocytic cells, osteoblasts, and neuroblastoma cells. Of these, 32 clones contain novel cDNA sequences which were not found in the GenBank database.

A large number of cDNA clones obtained by this procedure were found to represent 92 kDa type IV collagenase (gelatinase B; E.C. 3.4.24.35) as well as tartrate resistant acid phosphatase. In situ hybridization localized mRNAIfor gelatinase B to multinucleated giant cells in human osteoclastomas. Gelatinase B immunoreactivity was demonstrated in giant cells from 8/8 osteoclastomas, osteoclasts in normal bone, and in osteoclasts of Paget's disease by use of a polyclonal antisera raised against a synthetic gelatinase B peptide. In contrast, no immunoreactivity for 72 kDa type IV collagenase (gelatinase A; E.C. 3.4.24.24), which is the product of a separate gene, was detected in osteoclastomas or normal osteoclasts.

The present invention has utility for the production and identification of nucleic acid probes useful for identifying osteoclast-specific or -related DNA. Osteoclast-specific or -related DNA of the present invention can be used to express osteoclast-specific or -related gene products useful in the therapeutic treatment of disorders involving aberrant bone resorption. The osteoclast-specific or -related sequences are also useful for generating peptides which can then be used to produce antibodies useful for identifying osteoclast-specific or -related gene products, or for altering the activity of osteoclast-specific or -related gene products. Such antibodies are referred to as osteoclast-specific antibodies. Osteoclast-specific antibodies are also useful for identifying osteoclasts. Finally, osteoclast -specific or -related DNA sequences of the present invention are useful in gene therapy. For example, they can be used to alter the expression in osteoclasts of an aberrant osteoclast -specific or -related gene product or to correct aberrant expression of an osteoclast-specific or -related gene product. The sequences described herein can further be used to cause osteoclast-specific or -related gene expression in cells in which such expression does not ordinarily occur, i.e., in cells which are not osteoclasts.

EXAMPLE 1

Osteclast cDNA Library Construction

Messenger RNA (mRNA) obtained from a human osteoclastoma ('giant cell tumor of bone'), was used to construct an osteoclastoma cDNA library. Osteoclastomas are actively bone resorptive tumors, but are usually non-metastatic. In cryostat sections, osteoclastomas consist of ~30% multinucleated cells positive for tartrate resistant acid phosphatase (TRAP), a widely utilized phenotypic marker specific in vivo for osteoclasts (Minkin, *Calcif. Tissue Int.* 34:285–290 (1982)). The remaining cells are uncharacterized 'stromal' cells, a mixture of cell types with fibroblastic/mesenchymal morphology. Although it has not yet been definitively shown, it is generally held that the osteoclasts in these tumors are non-transformed, and are activated to resorb bone in vivo by substance(s) produced by the stromal cell element.

Monoclonal antibody reagents were used to partially characterize the surface phenotype of the multinucleated cells in the giant cell tumors of long bone. In frozen sections, all multinucleated cells expressed CD68, which has previously been reported to define an antigen specific for both osteoclasts and macrophages (Horton, M. A. and M. H. Helfrich, In Biology and Physiology of the Osteoclast, B. R. Rifkin and C. V. Gay, editors, CRC Press, Inc. Boca Raton, Fla., 33–54 (1992)). In contrast, no staining of giant cells was observed for CD11b or CD14 surface antigens, which are present on monocyte/macrophages and granulocytes (Arnaout, M. A. et al. *J. Cell. Physiol.* 137:305 (1988); Haziot, A. et al. *J. Immunol.* 141:547 (1988)). Cytocentrifuge preparations of human peripheral blood monocytes were positive for CD68, CD11b, and CD14. These results demonstrate that the multinucleated giant cells of osteoclastomas have a phenotype which is distinct from that of macrophages, and which is consistent with that of osteoclasts.

Osteoclastoma tissue was snap frozen in liquid nitrogen and used to prepare poly A⁺ mRNA according to standard methods. cDNA cloning into a pcDNAII vector was carried out using a commercially-available kit (Librarian, InVitrogen). Approximately $2.6 \times 10^6$ clones were obtained, >95% of which contained inserts of an average length 0.6 kB.

EXAMPLE 2

Stromal Cell mRNA Preparation

A portion of each osteoclastoma was snap frozen in liquid nitrogen for mRNA preparation. The remainder of the tumor was dissociated using brief trypsinization and mechanical disaggregation, and placed into tissue culture. These cells were expanded in Dulbecco's MEM (high glucose, Sigma) supplemented with 10% newborn calf serum (MA Bioproducts), gentamycin (0.5 mg/ml), 1-glutamine (2 mM) and non-essential amino acids (0.1 mM) (Gibco). The stromal cell population was passaged at least five times, after which it showed a homogenous, fibroblastic looking cell population that contained no multinucleated cells. The stromal cells were mononuclear, tested negative for acid phosphatase, and tested variably alkaline phosphatase positive. These findings indicate that propagated stromal cells (i.e., stromal cells that are passaged in culture) are non-osteoclastic and non-activated.

EXAMPLE 3

Identification of DNA Encoding Osteoclastoma-Specific or -Related Gene Products by Differential Screening of an osteoclastoma cDNA Library A total of 12,000 clones drawn from the osteoclastoma cDNA library were screened by differential hybridization, using mixed $^{32}$p labelled cDNA probes derived from (1) giant cell tumor mRNA (stromal cell$^+$, OC$^+$) and (2) mRNA from stromal cells (stromal cell$^+$, OC$^-$) cultivated from the same tumor. The probes were labelled with $^{32}$[P]dCTP by random priming to an activity of ~10$^9$CPM/μg. Of these 12,000 clones, 195 gave a positive hybridization signal with giant cell (i.e., osteoclast and stromal cell) mRNA, but not with stromal cell mRNA. Additionally, these clones failed to hybridize to cDNA produced from mRNA derived from a variety of unrelated human cell types including epithelial cells, fibroblasts, lymphocytes, myelomonocytic cells, osteoblasts, and neuroblastoma cells. The failure of these clones to hybridize to cDNA produced from mRNA derived from other cell types supports the conclusion that these clones are either uniquely expressed in osteoclasts, or are osteoclast-related.

The osteoclast (OC) cDNA library was screened for differential hybridization to OC cDNA (stromal cell$^+$, OC$^+$) and stromal cell cDNA (stromal cell$^+$, OC$^{31}$) as follows:

NYTRAN filters (Schleicher & Schuell) were placed on agar plates containing growth medium and ampicillin. Individual bacterial colonies from the OC library were randomly picked and transferred, in triplicate, onto filters with preruled grids and then onto a master agar plate. Up to 200 colonies were inoculated onto a single 90-mm filter/plate using these techniques. The plates were inverted and incubated at 37° C. until the bacterial inoculates had grown (on the filter) to a diameter of 0.5–1.0 mm.

The colonies were then lysed, and the DNA bound to the filters by first placing the filters on top of two pieces of Whatman 3 MM paper saturated with 0.5N NaOH for 5 minutes. The filters were neutralized by placing on two pieces of Whatman 3 MM paper saturated with 1M Tris-HCL, pH 8.0 for 3–5 minutes. Neutralization was followed by incubation on another set of Whatman 3 MM papers saturated with 1M Tris-HCL, pH 8.0/1.5 M NaCl for 3–5 minutes. The filters were then washed briefly in 2× SSC.

DNA was immobilized on the filters by baking the filters at 80° C. for 30 minutes. Filters were best used immediately, but they could be stored for up to one week in a vacuum jar at room temperature.

Filters were prehybridized in 5–8 ml of hybridization solution per filter, for 2–4 hours in a heat sealable bag. An additional 2 ml of solution was added for each additional filter added to the hybridization bag. The hybridization buffer consisted of 5× SSC, 5× Denhardt's solution, 1% SDS and 100 μg/ml denatured heterologous DNA.

Prior to hybridization, labeled probe was denatured by heating in 1× SSC for 5 minutes at 100° C., then immediately chilled on ice. Denatured probe was added to the filters in hybridization solution, and the filters hybridized with continuous agitation for 12–20 hours at 65° C.

After hybridization, the filters were washed in 2× SSC/0.2% SDS at 50°–60° C. for 30 minutes, followed by washing in 0.2× SSC/0.2% SDS at 60° C. for 60 minutes.

The filters were then air dried and autoradiographed using an intensifying screen at –70° C. overnight.

EXAMPLE 4

DNA SeqUencing of. Selected Clones

Clones reactive with the mixed tumor probe, but unreactive with the stromal cell probe, are expected to contain either osteoclast-related, or in vivo 'activated' stromal-cell-related gene products. One hundred and forty-four cDNA clones that hybridized to tumor cell cDNA, but not to stromal cell cDNA, were sequenced by the dideoxy chain termination method of Sanger et al. (Sanger F., et al. *Proc. Natl. Acad. Sci. USA* 74:5463 (1977)) using sequenase (US Biochemical). The DNASIS (Hitatchi) program was used to carry out sequence analysis and a homology search in the GenBank/EMBL database.

Fourteen of the 195 tumor$^+$ stromal$^-$ clones were identified as containing inserts with a sequence identical to the osteoclast marker, type 5 tartrate-resistant acid phosphatase (TRAP) (GenBank accession number J04430 M19534). The high representation of TRAP positive clones also indicates the effectiveness of the screening procedure in enriching for clones which contain osteoclast-specific or related cDNA sequences.

Interestingly, an even larger proportion of the tumor$^+$ stromal$^-$ clones (77/195; 39.5%) were identified as human gelatinase B (macrophage-derived gelatinase) (Wilhelm, S. M. *J. Biol. Chem.* 264:17213 (1989)), again indicating high expression of this enzyme by osteoclasts. Twenty-five of the gelatinase B clones were identified by dideoxy sequence analysis; all 25 showed 100% sequence homology to the published gelatinase B sequence (Genbank accession number J05070). The portions of the gelatinase B cDNA sequence covered by these clones is shown in the Figure (SEQ ID NO: 33). An additional 52 gelatinase B clones were identified by reactivity with a $^{32}$P-labelled probe for gelatinase B.

Thirteen of the sequenced clones yielded no readable sequence. A DNASIS search of GenBank/EMBL databases revealed that, of the remaining 91 clones, 32 clones contain novel sequences which have not yet been reported in the databases or in the literature. These partial sequences are presented in Table I. Note that three of these sequences were repeats, indicating fairly frequent representation of mRNA related to this sequence. The repeat sequences are indicated by $^{a,b}$, superscripts (Clones 198B, 223B and 32C of Table I).

TABLE I

PARTIAL SEQUENCES OF 32 NOVEL OC-SPECIFIC OR -RELATED
EXPRESSED GENES (cDNA CLONES)

```
34A  (SEQ ID NO: 1)
1    GCAAATATCT AAGTTTATTG CTTGGATTTC TAGTGAGAGC TGTTGAATTT GGTGATGTCA
61   AATGTTTCTA GGGTTTTTTT AGTTTGTTTT TATTGAAAAA TTTAATTATT TATGCTATAG
121  GTGATATTCT CTTTGAATAA ACCTATAATA GAAAATAGCA GCAGACAACA 4B   (SEQ ID NO: 2)
1    GTGTCAACCT GCATATCCTA AAAATGTCAA AATGCTGCAT CTGGTTAATG TCGGGGTAGG
61   GGG
```

TABLE I-continued

PARTIAL SEQUENCES OF 32 NOVEL OC-SPECIFIC OR -RELATED
EXPRESSED GENES (cDNA CLONES)

```
12B   (SEQ ID NO: 3)
1     CTTCCCTCTC TTGCTTCCCT TTCCCAAGCA GAGGTGCTCA CTCCATGGCC ACCGCCACCA
61    CAGGCCCACA GGGAGTACTG CCAGACTACT GCTGATGTTC TCTTAAGGCC CAGGGAGTCT
121   CAACCAGCTG GTGGTGAATG CTGCCTGGCA CGGGACCCCC CCC 28B   (SEQ ID NO: 4)
1     TTTTATTTGT AAATATATGT ATTACATCCC TAGAAAAAGA ATCCCAGGAT TTTCCCTCCT
61    GTGTGTTTTC GTCTTGCTTC TTCATGGTCC ATGATGCCAG CTGAGGTTGT CAGTACAATG
121   AAACCAAACT GGCGGGATGG AAGCAGATTA TTCTGCCATT TTTCCAGGTC TTT 37B   (SEQ ID NO: 5)
1     GGCTGGACAT GGGTGCCCTC CACGTCCCTC ATATCCCCAG GCACACTCTG GCCTCAGGTT
61    TTGCCCTGGC CATGTCATCT ACCTGGAGTG GGCCCTCCCC TTCTTCAGCC TTGAATCAAA
121   AGCCACTTTG TTAGGCGAGG ATTTCCCAGA CCACTCATCA CATTAAAAAA TATTTTGAAA
181   ACAAAAAAAA AAAAAAA 55B   (SEQ ID NO: 6)
1     TTGACAAAGC TGTTTATTTC CACCAATAAA TAGTATATGG TGATTGGGGT TTCTATTTAT
61    AAGAGTAGTG GCTATTATAT GGGGTATCAT GTTGATGCTC ATAAATAGTT CATATCTACT
121   TAATTTGCCT TC 60B   (SEQ ID NO: 7)
1     GAAGAGAGTT GTATGTACAA CCCCAACAGG CAAGGCAGCT AAATGCAGAG GGTACAGAGA
61    GATCCCGAGG GAATT 86B   (SEQ ID NO: 8)
1     GGATGGAAAC ATGTAGAAGT CCAGAGAAAA ACAATTTTAA AAAAAGGTGG AAAAGTTACG
61    GCAAACCTGA GATTTCAGCA TAAAATCTTT AGTTAGAAGT GAGAGAAAGA AGAGGGAGGC
121   TGGTTGCTGT TGCACGTATC AATAGGTTAT C 87B   (SEQ ID NO: 9)
1     TTCTTGATCT TTAGAACACT ATGAATAGGG AAAAAAAAAA AAACTGTTCA AAATAAAATG
61    TAGGAGCCGT GCTTTTGGAA TGCTTGAGTG AGGAGCTCAA CAAGTCCTCT CCCAAGAAAG
181   CAATGATAAA ACTTGACAAA A 98B   (SEQ ID NO: 10)
1     ACCCATTTCT AACAATTTTT ACTGTAAAAT TTTTGGTCAA AGTTCTAAGC TTAATCACAT
61    CTCAAAGAAT AGAGGCAATA TATAGCCCAT CTTACTAGAC ATACAGTATT AAACTGGACT
121   GAATATGAGG ACAAGCTCTA GTGGTCATTA AACCCCTCAG AA 110B  (SEQ ID NO: 11)
1     ACATATATTA ACAGCATTCA TTTGGCCAAA ATCTACACGT TTGTAGAATC CTACTGTATA
61    TAAAGTGGGA ATGTATCAAG TATAGACTAT GAAAGTGCAA ATAACAAGTC AAGGTTAGAT
121   TAACTTTTTT TTTTTACATT ATAAAATTAA CTTGTTT 118B  (SEQ ID NO: 12)
1     CCAAATTTCT CTGGAATCCA TCCTCCCTCC CATCACCATA GCCTCGAGAC GTCATTTCTG
61    TTTGACTACT CCAGC 133B  (SEQ ID NO: 13)
1     AACTAACCTC CTCGGACCCC TGCCTCACTC ATTTACACCA ACCACCCAAC TATCTATAAA
61    CCTGAGCCAT GGCCATCCCT TATGAGCGGC GCAGTGATTA TAGGCTTTCG CTCTAAGATA
121   AAAT 140B  (SEQ ID NO: 14)
1     ATTATTATTC TTTTTTTATG TTAGCTTAGC CATGCAAAAT TTACTGGTGA AGCAGTTAAT
61    AAAACACACA TCCCATTGAA GGGTTTTGTA CATTTCAGTC CTTACAAATA ACAAAGCAAT
121   GATAAACCCG GCACGTCCTG ATAGGAAATT C 144B  (SEQ ID NO: 15)
1     CGTGACACAA ACATGCATTC GTTTTATTCA TAAAACAGCC TGGTTTCCTA AAACAATACA
61    AACAGCATGT TCATCAGCAG GAAGCTGGCC GTGGGCAGGG GGGCC

198Bᵃ (SEQ ID NO: 16)
1     ATAGGTTAGA TTCTCATTCA CGGGACTAGT TAGCTTTAAG CACCCTAGAG GACTAGGGTA
61    ATCTGACTTC TCACTTCCTA AGTTCCCTCT TATATCCTCA AGGTAGAAAT GTCTATGTTT
121   TCTACTCCAA TTCATAAATC TATTCATAAG TCTTTGGTAC AAGTTACATG ATAAAAAGAA
181   ATGTGATTTG TCTTCCCTTC TTTGCACTTT TGAAATAAAG TATTTATCTC CTGTCTACAG
241   TTTAAT 212B  (SEQ ID NO: 17)
1     GTCCAGTATA AAGGAAAGCG TTAAGTCGGT AAGCTAGAGG ATTGTAAATA TCTTTTATGT
61    CCTCTAGATA AAACACCCGA TTAACAGATG TTAACCTTTT ATGTTTTGAT TTGCTTTAAA
121   AATGGCCTTC TACACATTAG CTCCAGCTAA AAAGACACAT TGAGAGCTTA GAGGATAGTC
181   TCTGGAGC
```

TABLE I-continued

PARTIAL SEQUENCES OF 32 NOVEL OC-SPECIFIC OR -RELATED EXPRESSED GENES (cDNA CLONES)

```
223B^b   (SEQ ID NO: 18)
1        GCACTTGGAA GGGAGTTGGT GTGCTATTTT TGAAGCAGAT GTGGTGATAC TGAGATTGTC
61       TGTTCAGTTT CCCCATTTGT TTGTGCTTCA AATGATCCTT CCTACTTTGC TTCTCTCCAC
121      CCATGACCTT TTTCACTGTG GCCATCAAGG ACTTTCCTGA CAGCTTGTGT ACTCTTAGGC
181      TAAGAGATGT GACTACAGCC TGCCCCTGAC TG 241B     (SEQ ID NO: 19)
1        TGTTAGTTTT TAGGAAGGCC TGTCTTCTGG GAGTGAGGTT TATTAGTCCA CTTCTTGGAG
61       CTAGACGTCC TATAGTTAGT CACTGGGGAT GGTGAAAGAG GGAGAAGAGG AAGGGCGAAG
121      GGAAGGGCTC TTTGCTAGTA TCTCCATTTC TAGAAGATGG TTTAGATGAT AACCACAGGT
181      CTATATGAGC ATAGTAAGGC TGT

32c^b    (SEQ ID NO: 20)
1        CCTATTTCTG ATCCTGACTT TGGACAAGGC CCTTCAGCCA GAAGACTGAC AAAGTCATCC
121      TCCGTCTACC AGAGCGTGCA CTTGTGATCC TAAAATAAGC TTCATCTCCG GCTGTGCCTT
161      GGGTGGAAGG GGCAGGATTC TGCAGCTGCT TTTGCATTTC TCTTCCTAAA TTTCATT 34c      (SEQ ID NO: 21)
1        CGGAGCGTAG GTGTGTTTAT TCCTGTACAA ATCATTACAA AACCAAGTCT GGGGCAGTCA
61       CCGCCCCCAC CCATCACCCC AGTGCAATGG CTAGCTGCTG GCCTTT 47c      (SEQ ID NO: 22)
1        TTAGTTCAGT CAAAGCAGGC AACCCCCTTT GGCACTGCTG CCACTGGGGT CATGGCGGTT
61       GTGGCAGCTG GGGAGGTTTC CCCAACACCC TCCTCTGCTT CCCTGTGTGT CGGGGTCTCA
121      GGAGCTGACC CAGAGTGGA 65c      (SEQ ID NO: 23)
1        GCTGAATGTT TAAGAGAGAT TTTGGTCTTA AAGGCTTCAT CATGAAAGTG TACATGCATA
61       TGCAAGTGTG AATTACGTGG TATGGATGGT TGCTTGTTTA TTAACTAAAG ATGTACAGCA
121      AACTGCCCGT TTAGAGTCCT CTTAATATTG ATGTCCTAAC ACTGGGTCTG CTTATGC 79c      (SEQ ID NO: 24)
1        GGCAGTGGGA TATGGAATCC AGAAGGGAAA CAAGCACTGG ATAATTAAAA ACAGCTGGGG
61       AGAAAACTGG GGAAACAAAG GATATATCCT CATGGCTCGA AATAAGAACA ACGCCTGTGG
121      CATTGCCAAC CTGGCCAGCT TCCCCAAGAT GTGACTCCAG CCAGAAA 84c      (SEQ ID NO: 25)
1        GCCAGGGCGG ACCGTCTTTA TTCCTCTCCT GCCTCAGAGG TCAGGAAGGA GGTCTGGCAG
61       GACCTGCAGT GGGCCCTAGT CATCTGTGGC AGCGAAGGTG AAGGGACTCA CCTTGTCGCC
121      CGTGCCTGAG TAGAACTTGT TCTGGAATTC C 86c      (SEQ ID NO: 26)
1        AACTCTTTCA CACTCTGGTA TTTTTAGTTT AACAATATAT GTGTTGTGTC TTGGAAATTA
61       GTTCATATCA ATTCATATTG AGCTGTCTCA TTCTTTTTTT AATGGTCATA TACAGTAGTA
121      TTCAATTATA AGAATATATC CTAATACTTT TTAAAA 87c      (SEQ ID NO: 27)
1        GGATAAGAAA GAAGGCCTGA GGGCTAGGGG CCGGGGCTGG CCTGCGTCTC AGTCCTGGGA
61       CGCAGCAGCC CGCACAGGTT GAGAGGGGCA CTTCCTCTTG CTTAGGTTGG TGAGGATCTG
121      GTCCTGGTTG GCCGGTGGAG AGCCACAAAA 88c      (SEQ ID NO: 28)
1        CTGACCTTCG AGAGTTTGAC CTGGAGCCGG ATACCTACTG CCGCTATGAC TCGGTCAGCG
61       TGTTCAACGG AGCCGTGAGC GACGACTCCG GTGGGGAAGT TCTGCGGCGA T 89c      (SEQ ID NO: 29)
1        ATCCCTGGCT GTGGATAGTG CTTTTGTGTA GCAAATGCTC CCTCCTTAAG GTTATAGGGC
61       TCCCTGAGTT TGGGAGTGTG GAAGTACTAC TTAACTGTCT GTCCTGCTTG GCTGTCGTTA
121      TCGTTTTCTG GTGATGTTGT GCTAACAATA AGAATAC 101c     (SEQ ID NO: 30)
1        GGCTGGGCAT CCCTCTCCTC CTCCATCCCC ATACATCACC AGGTCTAATG TTTACAAACG
61       GTGCCAGCCC GGCTCTGAAG CCAAGGGCCG TCCGTGCCAC GGTGGCTGTG AGTATTCCTC
121      CGTTAGCTTT CCCATAAGGT TGGAGTATCT GC 112c     (SEQ ID NO: 31)
1        CCAACTCCTA CCGCGATACA GACCCACAGA GTGCCATCCC TGAGAGACCA GACCGCTCCC
161      CAATACTCTC CTAAAATAAA CATGAAGCAC 114c     (SEQ ID NO: 32)
1        CATGGATGAA TGTCTCATGG TGGGAAGGAA CATGGTACAT TTC
```

[a]Repeated 3 times
[b]Repeated 2 times

Sequence analysis of the $OC^+$ stromal cell$^-$ cloned DNA sequences revealed, in addition to the novel sequences, a number of previously-described genes. The known genes identified (including type 5 acid phosphatase, gelatinase B, cystatin C (13 clones), Alu repeat sequences (11 clones), creatnine kinase (6 clones) and others) are summarized in Table II. In situ hybridization (described below) directly demonstrated that gelatinase B mRNA is expressed in multi-nucleated osteoclasts and not in stromal cells. Although gelatinase B is a well-characterized protease, its expression at high levels in osteoclasts has not been previously described. The expression in osteoclasts of cystatin C, a cysteine protease inhibitor, is also unexpected. This finding has not yet been confirmed by in situ hybridization. Taken together, these results demonstrate that most of these identified genes are osteoclast-expressed, thereby confirming the effectiveness of the differential screening strategy for identifying DNA encoding osteoclast-specific or -related gene products. Therefore, novel genes identified by this method have a high probability of being OC-specific or-related.

In addition, a minority of the genes identified by this screen are probably not expressed by OCs (Table II). For example, type III collagen (6 clones), collagen type I (1 clone), dermatansulfate (1 clone), and type VI collagen (1 clone) are more likely to originate from the stromal cells or from osteoblastic cells which are present in the tumor. These cDNA sequences survive the differential screening process either because the cells which produce them in the tumor in vivo die out during the stromal cell propagation phase, or because they stop producing their product in vitro. These clones do not constitute more than 5–10% of the all sequences selected by differential hybridization.

TABLE II

SEQUENCE ANALYSIS OF CLONES ENCODING KNOWN SEQUENCES FROM AN OSTEOCLASTOMA cDNA LIBRARY

| | |
|---|---|
| Clones with Sequence Homology to Collagenase Type IV | 25 total |
| Clones with Sequence Homology to Type 5 Tartrate Resistant Acid Phosphatase | 14 total |
| Clones with Sequence Homology to Cystatin C: | 13 total |
| Clones with Sequence Homology to Alu-repeat Sequences | 11 total |
| Clones with Sequence Homology to Creatnine Kinase | 6 total |
| Clones with Sequence Homology to Type III Collagen | 6 total |
| Clones with Sequence Homology to MHC Class I γ Invariant Chain | 5 total |
| Clones with Sequence Homology to MHC Class II β Chain | 3 total |
| One or Two Clone(s) with Sequence Homology to Each of the Following: | 10 total |
| αI collagen type I | |
| γ interferon inducible protein | |
| osteopontin | |
| Human chondroitin/dermatansulfate | |
| α globin | |
| β glucosidase/sphingolipid activator | |
| Human CAPL protein (Ca binding) | |
| Human EST 01024 | |
| Type VI collagen | |
| Human EST 00553 | |

EXAMPLE 5

In situ Hybridization of OC-Expressed Genes

In situ hybridization was performed using probes derived from novel cloned sequences in order to determine whether the novel putative OC-specific or -related genes are differentially expressed in osteoclasts (and not expressed in the stromal cells) of human giant cell tumors. Initially, in situ hybridization was performed using antisense (positive)and sense (negative control) cRNA probes against human type IV collagenase/gelatinase B labelled with $^{35}$S-UTP.

A thin section of human giant cell tumor reacted with the antisense probe resulted in intense labelling of all OCs, as indicated by the deposition of silver grains over these cells, but failed to label the stromal cell elements. In contrast, only minimal background labelling was observed with the sense (negative control) probe. This result confirmed that gelatinase B is expressed in human OCs.

In situ hybridization was then carried out using cRNA probes derived from 11/32 novel genes, labelled with digoxigenin UTP according to known methods.

The results of this analysis are summarized in Table III. Clones 28B, 118B, 140B, 198B, and 212B all gave positive reactions with OCs in frozen sections of a giant cell tumor, as did the positive control gelatinase B. These novel clones therefore are expressed in OCs and fulfill all criteria for OC-relatedness. 198B is repeated three times, indicating relatively high expression. Clones 4B, 37B, 88C and 98B produced positive reactions with the tumor tissue; however the signal was not well-localized to OCs. These clones are therefore not likely to be useful and are eliminated from further consideration. Clones 86B and 87B failed to give a positive reaction with any cell type, possibly indicating very low level expression. This group of clones could still be useful but may be difficult to study further. The results of this analysis show that 5/11 novel genes are expressed in OCs, indicating that ~50% of novel sequences likely to be OC-related.

To generate probes for the in situ hybridizations, cDNA derived from novel cloned osteoclast-specific or -related cDNA was subcloned into a BlueScript II SK(–) vector. The orientation of cloned inserts was determined by restriction analysis of subclones. The T7 and T3 promoters in the BlueScriptII vector was used to generate $^{35}$S-labelled ($^{35}$S-UTP, 850 Ci/mmol, Amersham, Arlington Heights, Ill.), or UTP digoxygenin labelled cRNA probes.

TABLE III

In Situ HYBRIDIZATION USING PROBES DERIVED FROM NOVEL SEQUENCES

| | Reactivity with: | |
|---|---|---|
| Clone | Osteoclasts | Stromal Cells |
| 4B (SEQ ID NO. 2) | + | + |
| 28B* (SEQ ID NO. 4) | + | – |
| 37B (SEQ ID NO. 5) | + | + |
| 86B (SEQ ID NO. 8) | – | – |
| 87B (SEQ ID NO. 9) | – | – |
| 88C (SEQ ID NO. 28) | + | + |
| 98B (SEQ ID NO. 10) | + | + |
| 118B* (SEQ ID NO. 12) | + | – |
| 140B* (SEQ ID NO. 14) | + | – |
| 198B* (SEQ ID NO. 16) | + | – |
| 212B* (SEQ ID NO. 17) | + | – |
| Gelatinase B* (SEQ ID NO. 33) | + | – |

*OC-expressed, as indicated by reactivity with antisense probe and lack of reactivity with sense probe on OCs only.

In situ hybridization was carried out on 7 micron cryostat sections of a human osteoclastoma as described previously (Chang, L.-C. et al. Cancer Res. 49:6700 (1989)). Briefly, tissue was fixed in 4% paraformaldehyde and embedded in OCT (Miles Inc., Kankakee, Ill. ). The sections were rehydrated, postfixed in 4% paraformaldehyde, washed, and pretreated with 10 mM DTT, 10 mM iodoacetamide, 10 mM N-ethylmaleimide and 0.1 triethanolamine-HCL. Prehybridization was done with 50% deionized formamide, 10 mM Tris-HCl, pH 7.0, 1× Denhardt's, 500 mg/ml tRNA, 80 mg/ml salmon sperm DNA, 0.3M NaCl 1 mM EDTA, and 100 mM DTT at 45° C. for 2 hours. Fresh hybridization solution containing 10% dextran sulfate and 1.5 ng/ml $^{35}$S-labelled or digoxygenin labelled RNA probe was applied after heat denaturation. Sections were coverslipped and then incubated in a moistened chamber at 45°–50° C. overnight. Hybridized sections were washed four times with 50% formamide, 2× SSC, containing 10 mM DTT and 0.5% Triton X-100 at 45° C. Sections were treated with RNase A and RNase T1 to digest single-stranded RNA, washed four times in 2× SSC/10 mM DTT.

In order to detect $^{35}$S-labelling by autoradiography, slides were dehydrated, dried, and coated with Kodak NTB-2 emulsion. The duplicate slides were split, and each set was placed in a black box with desiccant, sealed, and incubated at 4° C. for 2 days. The slides were developed (4 minutes) and fixed (5 minutes) using Kodak developer D19 and Kodak fixer. Hematoxylin and eosin were used as counterstains.

In order to detect digoxygenin-labelled probes, a Nucleic Acid Detection Kit (Boehringer-Mannheim, Cat. #1175041) was used. Slides were washed in Buffer 1 consisting of 100 mM Tris/150 mM NaCl, pH7.5, for 1 minute. 100 µl Buffer 2 was added (made by adding 2 mg/ml blocking reagent as provided by the manufacturer) in Buffer 1 to each slide. The slides were placed on a shaker and gently swirled at 20° C.

Antibody solutions were diluted 1:100 with Buffer 2 (as provided by the manufacturer). 100 µl of diluted antibody solution was applied to the slides and the slides were then incubated in a chamber for 1 hour at room temperature. The slides were monitored to avoid drying. After incubation with antibody solution, slides were washed in Buffer 1 for 10 minutes, then washed in Buffer 3 containing 2 mM levamisole for 2 minutes.

After washing, 100 µl color solution was added to the slides. Color solution consisted of nitroblue/tetrazolium salt (NBT) (1:225 dilution) 4.5 µl, 5-bromo-4-chloro-3-indolyl phosphate (1:285 dilution) 3.5 µl levamisole 0.2 mg in Buffer 3 (as provided by the manufacturer) in a total volume of 1 ml. Color solution was prepared immediately before use.

After adding the color solution, the slides were placed in a dark, humidified chamber at 20° C. for 2–5 hours and monitored for color development. The color reaction was stopped by rinsing slides in TE Buffer.

The slides were stained for 60 seconds in 0.25% methyl green, washed with tap water, then mounted with water-based Permount (Fisher).

EXAMPLE 6

Immunohistochemistry

Immunohistochemical staining was performed on frozen and paraffin embedded tissues as well as on cytospin preparations (see Table IV). The following antibodies were used: polyclonal rabbit anti-human gelatinase antibodies; Ab110 for gelatinase B; monoclonal mouse anti-human CD68 antibody (clone KP1) (DAKO, Denmark); (anti-CD11b) and Mo2 (anti-CD14) derived from ATCC cell lines HB CRL 8026 and TIB 228/HB44. The anti-human gelatinase B antibody Ab11O was raised against a synthetic peptide with the amino acid sequence EALMYPMYRFTEGPPLHK (SEQ ID NO: 34), which is specific for human gelatinase B (Corcoran, M. L. et al. *J. Biol. Chem.* 267:515 (1992)).

Detection of the immunohistochemical staining was achieved by using a goat anti-rabbit glucose oxidase kit (Vector Laboratories, Burlingame Calif.) according to the manufacturer's directions. Briefly, the sections were rehydrated and pretested with either acetone or 0.1% trypsin. Normal goat serum was used to block nonspecific binding. Incubation with the primary antibody for 2 hours or overnight (Ab110: 1/500 dilution) was followed by either a glucose oxidase labeled secondary anti-rabbit serum, or, in the case of the mouse monoclonal antibodies, were reacted with purified rabbit anti-mouse Ig before incubation with the secondary antibody.

Paraffin embedded and frozen sections from osteoclastomas (GCT) were reacted with a rabbit antiserum against gelatinase B (antibody 110) (Corcoran, M. L. et al. *J. Biol. Chem.* 267:515 (1992)), followed by color development with glucose oxidase linked reagents. The osteoclasts of a giant cell tumor were uniformly strongly positive for gelatinase B, whereas the stromal cells were unreactive. Control sections reacted with rabbit preimmune serum were negative. Identical findings were obtained for all 8 long bone giant cell tumors tested (Table IV). The osteoclasts present in three out of four central giant cell granulomas (GCG) of the mandible were also positive for gelatinase B expression. These neoplasms are similar but not identical to the long bone giant cell tumors, apart from their location in the jaws (Shafer, W. G. et al., Textbook of Oral Pathology, W. B. Saunders Company, Philadelphia, pp. 144–149 (1983)). In contrast, the multinucleated cells from a peripheral giant cell tumor, which is a generally non-resorptive tumor of oral soft tissue, were unreactive with antibody 110 (Shafer, W. G. et al., Textbook of Oral Pathology, W. B. Saunders Company, Philadelphia, pp. 144–149 (1983)).

Antibody 110 was also utilized to assess the presence of gelatinase B in normal bone (n=3) and in Paget's disease, in which there is elevated bone remodeling and increased osteoclastic activity. Strong staining for gelatinase B was observed in osteoclasts both in normal bone (mandible of a 2 year old), and in Paget's disease. Staining was again absent in controls incubated with preimmune serum. Osteoblasts did not stain in any of the tissue sections, indicating that gelatinase B expression is limited to osteoclasts in bone. Finally, peripheral blood monocytes were also reactive with antibody 110 (Table IV).

TABLE IV

DISTRIBUTION OF GELATINASE B IN VARIOUS TISSUES

| Samples | Antibodies tested Ab 110 gelatinase B |
|---|---|
| GCT frozen (n = 2) | |
| giant cells | + |
| stromal cells | − |
| GCT paraffin (n = 6) | |
| giant cells | + |
| stromal cells | − |
| central GCG (n = 4) | |
| giant cells | + (¾) |
| stromal cells | − |
| peripheral GCT (n = 4) | |
| giant cells | − |
| stromal cells | − |
| Paget's disease (n = 1) | |
| osteoclasts | + |
| osteoblasts | − |

TABLE IV-continued

DISTRIBUTION OF GELATINASE B IN VARIOUS TISSUES

| Samples | Antibodies tested Ab 110 gelatinase B |
|---|---|
| normal bone (n = 3) | |
| osteoclasts | + |
| osteoblasts | − |
| monocytes (cytospin) | + |

Distribution of gelatinase B in multinucleated giant cells, osteoclasts, osteoblasts and stromal cells in various tissues. In general, paraffin embedded tissues were used for these experiments; exceptions are indicated.

Equivalents

Those skilled in the art will recognize, or be able to ascertain using no more than routine experimentation, many equivalents to the specific embodiments described herein. Such equivalents are intended to be encompassed by the following claims.

---

We claim:

1. A method of identifying DNA encoding an osteoclast-specific or -related gene product, comprising the steps of:

a) contacting a sample containing DNA with a stromal cell+, osteoclast+probe under conditions appropriate for hybridization of the probe to the DNA;

b) contacting said sample with a stromal cell+, osteoclast–probe under conditions appropriate for hybridization of the stromal cell+, osteoclast–probe to the DNA; and c) identifying DNA which hybridizes to the stromal cell+, osteoclast+probe, but does not hybridize to the stromal cell+, osteoclast–probe, thereby identifying DNA encoding an osteoclast-specific or -related gene product.

2. A method of claim 1 wherein the probe is a nucleic acid probe.

3. A method of identifying DNA encoding an osteoclast-specific or -related gene product, comprising the steps of:

a) contacting a sample containing DNA with cDNA or mRNA from an osteoclastoma under conditions appropriate for hybridization of the DNA with the cDNA or mRNA from an osteoclastoma;

b) contacting said sample with cDNA or mRNA from stromal cells cultured from an osteoclastoma under conditions appropriate for hybridization of the DNA with the cDNA or mRNA from said stromal cells; and c) identifying DNA which hybridizes with cDNA or mRNA from an osteoclastoma but does not hybridize with cDNA or mRNA from the stromal cells cultured from an osteoclastoma, thereby identifying DNA encoding an osteoclast-specific or -related gene product.

\* \* \* \* \*

UNITED STATES PATENT AND TRADEMARK OFFICE
CERTIFICATE OF CORRECTION

PATENT NO. : 5,624,801
DATED : April 29, 1997
INVENTOR(S) : Philip Stashenko, Yi-Ping Li and Anne L. Wucherpfennig It is certified that error appears in the above-indentified patent and that said Letters Patent is hereby corrected as shown below:

On the title page: Item [54] and Column 1, line 1, delete "Related" and insert -- -Related--;

Column 1, line 4, "Related Applications": insert the following paragraph:

--GOVERNMENT FUNDING

This invention was made with Government support under Grant No. DE07378 awarded by the National Institutes of Health, National Institute for Dental Research. The Government has certain rights in the invention.--

UNITED STATES PATENT AND TRADEMARK OFFICE
CERTIFICATE OF CORRECTION

PATENT NO. : 5,624,801
DATED : April 29, 1997
INVENTOR(S) : Philip Stashenko, Yi-Ping Li and Anne L. Wucherpfennig It is certified that error appears in the above-indentified patent and that said Letters Patent is hereby corrected as shown below:

Column 33,

Claim 1, line 31: delete "osteoclast+probe" and insert --osteoclast⁺ probe--;

Claim 1, line 35: delete "osteoclast-probe" and insert --osteoclast⁻ probe--;

Claim 1, line 37: delete "osteoclast+probe" and insert --osteoclast⁺ probe--;

Claim 1, line 38: delete "osteoclast-probe" and insert --osteoclast⁻ probe--.

Signed and Sealed this

Nineteenth Day of August, 1997

Attest:

BRUCE LEHMAN

*Attesting Officer*    Commissioner of Patents and Trademarks

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 170 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
GCAAATATCT AAGTTTATTG CTTGGATTTC TAGTGAGAGC TGTTGAATTT GGTGATGTCA        60
AATGTTTCTA GGGTTTTTTT AGTTTGTTTT TATTGAAAAA TTTAATTATT TATGCTATAG       120
GTGATATTCT CTTTGAATAA ACCTATAATA GAAATAGCA GCAGACAACA                   170
```

( 2 ) INFORMATION FOR SEQ ID NO:2:

( i ) SEQUENCE CHARACTERISTICS:
        ( A ) LENGTH: 63 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

```
GTGTCAACCT GCATATCCTA AAAATGTCAA AATGCTGCAT CTGGTTAATG TCGGGGTAGG        60
GGG                                                                      63
```

( 2 ) INFORMATION FOR SEQ ID NO:3:

( i ) SEQUENCE CHARACTERISTICS:
        ( A ) LENGTH: 163 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
CTTCCCTCTC  TTGCTTCCCT  TTCCCAAGCA  GAGGTGCTCA  CTCCATGGCC  ACCGCCACCA      60

CAGGCCCACA  GGGAGTACTG  CCAGACTACT  GCTGATGTTC  TCTTAAGGCC  CAGGGAGTCT     120

CAACCAGCTG  GTGGTGAATG  CTGCCTGGCA  CGGGACCCCC  CCC                        163
```

( 2 ) INFORMATION FOR SEQ ID NO:4:

( i ) SEQUENCE CHARACTERISTICS:
        ( A ) LENGTH: 173 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:4:

```
TTTTATTTGT  AAATATATGT  ATTACATCCC  TAGAAAAAGA  ATCCCAGGAT  TTTCCCTCCT      60

GTGTGTTTTC  GTCTTGCTTC  TTCATGGTCC  ATGATGCCAG  CTGAGGTTGT  CAGTACAATG     120

AAACCAAACT  GGCGGGATGG  AAGCAGATTA  TTCTGCCATT  TTTCCAGGTC  TTT            173
```

( 2 ) INFORMATION FOR SEQ ID NO:5:

( i ) SEQUENCE CHARACTERISTICS:
        ( A ) LENGTH: 197 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:5:

```
GGCTGGACAT  GGGTGCCCTC  CACGTCCCTC  ATATCCCCAG  GCACACTCTG  GCCTCAGGTT      60

TTGCCCTGGC  CATGTCATCT  ACCTGGAGTG  GGCCCTCCCC  TTCTTCAGCC  TTGAATCAAA     120

AGCCACTTTG  TTAGGCGAGG  ATTTCCCAGA  CCACTCATCA  CATTAAAAAA  TATTTTGAAA     180

ACAAAAAAAA  AAAAAAA                                                        197
```

( 2 ) INFORMATION FOR SEQ ID NO:6:

( i ) SEQUENCE CHARACTERISTICS:
        ( A ) LENGTH: 132 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

```
TTGACAAAGC  TGTTTATTTC  CACCAATAAA  TAGTATATGG  TGATTGGGGT  TTCTATTTAT      60

AAGAGTAGTG  GCTATTATAT  GGGGTATCAT  GTTGATGCTC  ATAAATAGTT  CATATCTACT     120

TAATTTGCCT  TC                                                             132
```

( 2 ) INFORMATION FOR SEQ ID NO:7:

( i ) SEQUENCE CHARACTERISTICS:
        ( A ) LENGTH: 75 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:7:

```
GAAGAGAGTT  GTATGTACAA  CCCCAACAGG  CAAGGCAGCT  AAATGCAGAG  GGTACAGAGA      60
```

GATCCCGAGG GAATT 75

( 2 ) INFORMATION FOR SEQ ID NO:8:

( i ) SEQUENCE CHARACTERISTICS:
        ( A ) LENGTH: 151 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:8:

GGATGGAAAC ATGTAGAAGT CCAGAGAAAA ACAATTTTAA AAAAAGGTGG AAAAGTTACG 60

GCAAACCTGA GATTTCAGCA TAAAATCTTT AGTTAGAAGT GAGAGAAAGA AGAGGGAGGC 120

TGGTTGCTGT TGCACGTATC AATAGGTTAT C 151

( 2 ) INFORMATION FOR SEQ ID NO:9:

( i ) SEQUENCE CHARACTERISTICS:
        ( A ) LENGTH: 141 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:9:

TTCTTGATCT TTAGAACACT ATGAATAGGG AAAAAGAAA AAACTGTTCA AAATAAAATG 60

TAGGAGCCGT GCTTTTGGAA TGCTTGAGTG AGGAGCTCAA CAAGTCCTCT CCCAAGAAAG 120

CAATGATAAA ACTTGACAAA A 141

( 2 ) INFORMATION FOR SEQ ID NO:10:

( i ) SEQUENCE CHARACTERISTICS:
        ( A ) LENGTH: 162 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:10:

ACCCATTTCT AACAATTTTT ACTGTAAAAT TTTTGGTCAA AGTTCTAAGC TTAATCACAT 60

CTCAAAGAAT AGAGGCAATA TATAGCCCAT CTTACTAGAC ATACAGTATT AAACTGGACT 120

GAATATGAGG ACAAGCTCTA GTGGTCATTA AACCCCTCAG AA 162

( 2 ) INFORMATION FOR SEQ ID NO:11:

( i ) SEQUENCE CHARACTERISTICS:
        ( A ) LENGTH: 157 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:11:

ACATATATTA ACAGCATTCA TTTGGCCAAA ATCTACACGT TTGTAGAATC CTACTGTATA 60

TAAAGTGGGA ATGTATCAAG TATAGACTAT GAAAGTGCAA ATAACAAGTC AAGGTTAGAT 120

TAACTTTTTT TTTTACATT ATAAAATTAA CTTGTTT 157

( 2 ) INFORMATION FOR SEQ ID NO:12:

( i ) SEQUENCE CHARACTERISTICS:
        ( A ) LENGTH: 75 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:12:

```
CCAAATTTCT CTGGAATCCA TCCTCCCTCC CATCACCATA GCCTCGAGAC GTCATTTCTG      60
TTTGACTACT CCAGC                                                      75
```

( 2 ) INFORMATION FOR SEQ ID NO:13:

( i ) SEQUENCE CHARACTERISTICS:
        ( A ) LENGTH: 124 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

```
AACTAACCTC CTCGGACCCC TGCCTCACTC ATTTACACCA ACCACCCAAC TATCTATAAA      60
CCTGAGCCAT GGCCATCCCT TATGAGCGGC GCAGTGATTA TAGGCTTTCG CTCTAAGATA     120
AAAT                                                                  124
```

( 2 ) INFORMATION FOR SEQ ID NO:14:

( i ) SEQUENCE CHARACTERISTICS:
        ( A ) LENGTH: 151 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:14:

```
ATTATTATTC TTTTTTATG TTAGCTTAGC CATGCAAAAT TTACTGGTGA AGCAGTTAAT       60
AAAACACACA TCCCATTGAA GGGTTTTGTA CATTTCAGTC CTTACAAATA ACAAAGCAAT     120
GATAAACCCG GCACGTCCTG ATAGGAAATT C                                    151
```

( 2 ) INFORMATION FOR SEQ ID NO:15:

( i ) SEQUENCE CHARACTERISTICS:
        ( A ) LENGTH: 105 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:15:

```
CGTGACACAA ACATGCATTC GTTTATTCA TAAAACAGCC TGGTTTCCTA AACAATACA        60
AACAGCATGT TCATCAGCAG GAAGCTGGCC GTGGGCAGGG GGCC                     105
```

( 2 ) INFORMATION FOR SEQ ID NO:16:

( i ) SEQUENCE CHARACTERISTICS:
        ( A ) LENGTH: 246 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:16:

| | | | | | |
|---|---|---|---|---|---|
| ATAGGTTAGA | TTCTCATTCA | CGGGACTAGT | TAGCTTTAAG | CACCCTAGAG | GACTAGGGTA | 60 |
| ATCTGACTTC | TCACTTCCTA | AGTTCCCTCT | TATATCCTCA | AGGTAGAAAT | GTCTATGTTT | 120 |
| TCTACTCCAA | TTCATAAATC | TATTCATAAG | TCTTTGGTAC | AAGTTACATG | ATAAAAGAA | 180 |
| ATGTGATTTG | TCTTCCCTTC | TTTGCACTTT | TGAAATAAAG | TATTTATCTC | CTGTCTACAG | 240 |
| TTTAAT | | | | | | 246 |

( 2 ) INFORMATION FOR SEQ ID NO:17:

( i ) SEQUENCE CHARACTERISTICS:
        ( A ) LENGTH: 188 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:17:

| | | | | | |
|---|---|---|---|---|---|
| GTCCAGTATA | AAGGAAAGCG | TTAAGTCGGT | AAGCTAGAGG | ATTGTAAATA | TCTTTTATGT | 60 |
| CCTCTAGATA | AAACACCCGA | TTAACAGATG | TTAACCTTTT | ATGTTTGAT | TTGCTTTAAA | 120 |
| AATGGCCTTC | TACACATTAG | CTCCAGCTAA | AAAGACACAT | TGAGAGCTTA | GAGGATAGTC | 180 |
| TCTGGAGC | | | | | | 188 |

( 2 ) INFORMATION FOR SEQ ID NO:18:

( i ) SEQUENCE CHARACTERISTICS:
        ( A ) LENGTH: 212 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:18:

| | | | | | |
|---|---|---|---|---|---|
| GCACTTGGAA | GGGAGTTGGT | GTGCTATTTT | TGAAGCAGAT | GTGGTGATAC | TGAGATTGTC | 60 |
| TGTTCAGTTT | CCCCATTTGT | TTGTGCTTCA | AATGATCCTT | CCTACTTTGC | TTCTCTCCAC | 120 |
| CCATGACCTT | TTCACTGTG | GCCATCAAGG | ACTTTCCTGA | CAGCTTGTGT | ACTCTTAGGC | 180 |
| TAAGAGATGT | GACTACAGCC | TGCCCCTGAC | TG | | | 212 |

( 2 ) INFORMATION FOR SEQ ID NO:19:

( i ) SEQUENCE CHARACTERISTICS:
        ( A ) LENGTH: 203 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:19:

| | | | | | |
|---|---|---|---|---|---|
| TGTTAGTTTT | TAGGAAGGCC | TGTCTTCTGG | GAGTGAGGTT | TATTAGTCCA | CTTCTTGGAG | 60 |
| CTAGACGTCC | TATAGTTAGT | CACTGGGGAT | GGTGAAAGAG | GGAGAAGAGG | AAGGGCGAAG | 120 |
| GGAAGGGCTC | TTTGCTAGTA | TCTCCATTTC | TAGAAGATGG | TTTAGATGAT | AACCACAGGT | 180 |
| CTATATGAGC | ATAGTAAGGC | TGT | | | | 203 |

( 2 ) INFORMATION FOR SEQ ID NO:20:

( i ) SEQUENCE CHARACTERISTICS:
    ( A ) LENGTH: 177 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:20:

| | | | | | |
|---|---|---|---|---|---|
| CCTATTTCTG | ATCCTGACTT | TGGACAAGGC | CCTTCAGCCA | GAAGACTGAC | AAAGTCATCC | 60 |
| TCCGTCTACC | AGAGCGTGCA | CTTGTGATCC | TAAAATAAGC | TTCATCTCCG | GCTGTGCCTT | 120 |
| GGGTGGAAGG | GGCAGGATTC | TGCAGCTGCT | TTTGCATTTC | TCTTCCTAAA | TTTCATT | 177 |

( 2 ) INFORMATION FOR SEQ ID NO:21:

( i ) SEQUENCE CHARACTERISTICS:
        ( A ) LENGTH: 106 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:21:

| | | | | | |
|---|---|---|---|---|---|
| CGGAGCGTAG | GTGTGTTTAT | TCCTGTACAA | ATCATTACAA | AACCAAGTCT | GGGGCAGTCA | 60 |
| CCGCCCCCAC | CCATCACCCC | AGTGCAATGG | CTAGCTGCTG | GCCTTT | | 106 |

( 2 ) INFORMATION FOR SEQ ID NO:22:

( i ) SEQUENCE CHARACTERISTICS:
        ( A ) LENGTH: 139 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:22:

| | | | | | |
|---|---|---|---|---|---|
| TTAGTTCAGT | CAAAGCAGGC | AACCCCTTT | GGCACTGCTG | CCACTGGGGT | CATGGCGGTT | 60 |
| GTGGCAGCTG | GGGAGGTTTC | CCCAACACCC | TCCTCTGCTT | CCCTGTGTGT | CGGGGTCTCA | 120 |
| GGAGCTGACC | CAGAGTGGA | | | | | 139 |

( 2 ) INFORMATION FOR SEQ ID NO:23:

( i ) SEQUENCE CHARACTERISTICS:
        ( A ) LENGTH: 177 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:23:

| | | | | | |
|---|---|---|---|---|---|
| GCTGAATGTT | TAAGAGAGAT | TTGGTCTTA | AAGGCTTCAT | CATGAAAGTG | TACATGCATA | 60 |
| TGCAAGTGTG | AATTACGTGG | TATGGATGGT | TGCTTGTTTA | TTAACTAAAG | ATGTACAGCA | 120 |
| AACTGCCCGT | TTAGAGTCCT | CTTAATATTG | ATGTCCTAAC | ACTGGGTCTG | CTTATGC | 177 |

( 2 ) INFORMATION FOR SEQ ID NO:24:

( i ) SEQUENCE CHARACTERISTICS:
        ( A ) LENGTH: 167 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:24:

| | | | | | |
|---|---|---|---|---|---|
| GGCAGTGGGA | TATGGAATCC | AGAAGGGAAA | CAAGCACTGG | ATAATTAAAA | ACAGCTGGGG | 60 |
| AGAAAACTGG | GGAAACAAAG | GATATATCCT | CATGGCTCGA | AATAAGAACA | ACGCCTGTGG | 120 |
| CATTGCCAAC | CTGGCCAGCT | TCCCCAAGAT | GTGACTCCAG | CCAGAAA | | 167 |

( 2 ) INFORMATION FOR SEQ ID NO:25:

( i ) SEQUENCE CHARACTERISTICS:
        ( A ) LENGTH: 151 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:25:

| | | | | | |
|---|---|---|---|---|---|
| GCCAGGGCGG | ACCGTCTTTA | TTCCTCTCCT | GCCTCAGAGG | TCAGGAAGGA | GGTCTGGCAG | 60 |
| GACCTGCAGT | GGGCCCTAGT | CATCTGTGGC | AGCGAAGGTG | AAGGGACTCA | CCTTGTCGCC | 120 |
| CGTGCCTGAG | TAGAACTTGT | TCTGGAATTC | C | | | 151 |

( 2 ) INFORMATION FOR SEQ ID NO:26:

( i ) SEQUENCE CHARACTERISTICS:
        ( A ) LENGTH: 156 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:26:

| | | | | | |
|---|---|---|---|---|---|
| AACTCTTTCA | CACTCTGGTA | TTTTAGTTT | AACAATATAT | GTGTTGTGTC | TTGGAAATTA | 60 |
| GTTCATATCA | ATTCATATTG | AGCTGTCTCA | TTCTTTTTTT | AATGGTCATA | TACAGTAGTA | 120 |
| TTCAATTATA | AGAATATATC | CTAATACTTT | TTAAAA | | | 156 |

( 2 ) INFORMATION FOR SEQ ID NO:27:

( i ) SEQUENCE CHARACTERISTICS:
        ( A ) LENGTH: 150 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:27:

| | | | | | |
|---|---|---|---|---|---|
| GGATAAGAAA | GAAGGCCTGA | GGGCTAGGGG | CCGGGGCTGG | CCTGCGTCTC | AGTCCTGGGA | 60 |
| CGCAGCAGCC | CGCACAGGTT | GAGAGGGCA | CTTCCTCTTG | CTTAGGTTGG | TGAGGATCTG | 120 |
| GTCCTGGTTG | GCCGGTGGAG | AGCCACAAAA | | | | 150 |

( 2 ) INFORMATION FOR SEQ ID NO:28:

( i ) SEQUENCE CHARACTERISTICS:
        ( A ) LENGTH: 212 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:28:

```
GCACTTGGAA GGGAGTTGGT GTGCTATTTT TGAAGCAGAT GTGGTGATAC TGAGATTGTC        60

TGTTCAGTTT CCCCATTTGT TTGTGCTTCA AATGATCCTT CCTACTTTGC TTCTCTCCAC       120

CCATGACCTT TTTCACTGTG GCCATCAAGG ACTTTCCTGA CAGCTTGTGT ACTCTTAGGC       180

TAAGAGATGT GACTACAGCC TGCCCCTGAC TG                                    212
```

( 2 ) INFORMATION FOR SEQ ID NO:29:

( i ) SEQUENCE CHARACTERISTICS:
        ( A ) LENGTH: 157 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:29:

```
ATCCCTGGCT GTGGATAGTG CTTTTGTGTA GCAAATGCTC CCTCCTTAAG GTTATAGGGC        60

TCCCTGAGTT TGGGAGTGTG GAAGTACTAC TTAACTGTCT GTCCTGCTTG GCTGTCGTTA       120

TCGTTTTCTG GTGATGTTGT GCTAACAATA AGAATAC                                157
```

( 2 ) INFORMATION FOR SEQ ID NO:30:

( i ) SEQUENCE CHARACTERISTICS:
        ( A ) LENGTH: 152 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:30:

```
GGCTGGGCAT CCCTCTCCTC CTCCATCCCC ATACATCACC AGGTCTAATG TTTACAAACG        60

GTGCCAGCCC GGCTCTGAAG CCAAGGGCCG TCCGTGCCAC GGTGGCTGTG AGTATTCCTC       120

CGTTAGCTTT CCCATAAGGT TGGAGTATCT GC                                    152
```

( 2 ) INFORMATION FOR SEQ ID NO:31:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:31:

```
CCAACTCCTA CCGCGATACA GACCCACAGA GTGCCATCCC TGAGAGACCA GACCGCTCCC        60

CAATACTCTC CTAAAATAAA CATGAAGCAC                                         90
```

( 2 ) INFORMATION FOR SEQ ID NO:32:

( i ) SEQUENCE CHARACTERISTICS:
        ( A ) LENGTH: 43 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:32:

```
CATGGATGAA TGTCTCATGG TGGGAAGGAA CATGGTACAT TTC                          43
```

( 2 ) INFORMATION FOR SEQ ID NO:33:

(i) SEQUENCE CHARACTERISTICS:
  (A) LENGTH: 2334 base pairs
  (B) TYPE: nucleic acid
  (C) STRANDEDNESS: double
  (D) TOPOLOGY: linear (ii) MOLECULE TYPE: other nucleic acid (xi) SEQUENCE DESCRIPTION: SEQ ID NO:33:

| | | | | | | |
|---|---|---|---|---|---|---|
| AGACACCTCT | GCCCTCACCA | TGAGCCTCTG | GCAGCCCTG | GTCCTGGTGC | TCCTGGTGCT | 60 |
| GGGCTGCTGC | TTTGCTGCCC | CCAGACAGCG | CCAGTCCACC | CTTGTGCTCT | TCCCTGGAGA | 120 |
| CCTGAGAACC | AATCTCACCG | ACAGGCAGCT | GGCAGAGGAA | TACCTGTACC | GCTATGGTTA | 180 |
| CACTCGGGTG | GCAGAGATGC | GTGGAGAGTC | GAAATCTCTG | GGGCCTGCGC | TGCTGCTTCT | 240 |
| CCAGAAGCAA | CTGTCCCTGC | CCGAGACCGG | TGAGCTGGAT | AGCGCCACGC | TGAAGGCCAT | 300 |
| GCGAACCCCA | CGGTGCGGGG | TCCCAGACCT | GGGCAGATTC | CAAACCTTTG | AGGGCGACCT | 360 |
| CAAGTGGCAC | CACCACAACA | TCACCTATTG | GATCCAAAAC | TACTCGGAAG | ACTTGCCGCG | 420 |
| GGCGGTGATT | GACGACGCCT | TTGCCCGCGC | CTTCGCACTG | TGGAGCGCGG | TGACGCCGCT | 480 |
| CACCTTCACT | CGCGTGTACA | GCCGGGACGC | AGACATCGTC | ATCCAGTTTG | GTGTCGCGGA | 540 |
| GCACGGAGAC | GGGTATCCCT | TCGACGGGAA | GGACGGGCTC | CTGGCACACG | CCTTTCCTCC | 600 |
| TGGCCCCGGC | ATTCAGGGAG | ACGCCCATTT | CGACGATGAC | GAGTTGTGGT | CCCTGGGCAA | 660 |
| GGGCGTCGTG | GTTCCAACTC | GGTTTGGAAA | CGCAGATGGC | GCGGCCTGCC | ACTTCCCCTT | 720 |
| CATCTTCGAG | GGCCGCTCCT | ACTCTGCCTG | CACCACCGAC | GGTCGCTCCG | ACGGGTTGCC | 780 |
| CTGGTGCAGT | ACCACGGCCA | ACTACGACAC | CGACGACCGG | TTTGGCTTCT | GCCCCAGCGA | 840 |
| GAGACTCTAC | ACCCGGGACG | GCAATGCTGA | TGGGAAACCC | TGCCAGTTTC | CATTCATCTT | 900 |
| CCAAGGCCAA | TCCTACTCCG | CCTGCACCAC | GGACGGTCGC | TCCGACGGCT | ACCGCTGGTG | 960 |
| CGCCACCACC | GCCAACTACG | ACCGGGACAA | GCTCTTCGGC | TTCTGCCCGA | CCCGAGCTGA | 1020 |
| CTCGACGGTG | ATGGGGGGCA | ACTCGGCGGG | GGAGCTGTGC | GTCTTCCCCT | TCACTTTCCT | 1080 |
| GGGTAAGGAG | TACTCGACCT | GTACCAGCGA | GGGCCGCGGA | GATGGGCGCC | TCTGGTGCGC | 1140 |
| TACCACCTCG | AACTTTGACA | GCGACAAGAA | GTGGGGCTTC | TGCCCGGACC | AAGGATACAG | 1200 |
| TTTGTTCCTC | GTGGCGGCGC | ATGAGTTCGG | CCACGCGCTG | GCTTAGATC | ATTCCTCAGT | 1260 |
| GCCGGAGGCG | CTCATGTACC | CTATGTACCG | CTTCACTGAG | GGGCCCCCT | TGCATAAGGA | 1320 |
| CGACGTGAAT | GGCATCCGGC | ACCTCTATGG | TCCTCGCCCT | GAACCTGAGC | CACGGCCTCC | 1380 |
| AACCACCACC | ACACCGCAGC | CCACGGCTCC | CCCGACGGTC | TGCCCCACCG | GACCCCCCAC | 1440 |
| TGTCCACCCC | TCAGAGCGCC | CCACAGCTGG | CCCCACAGGT | CCCCCCTCAG | CTGGCCCCAC | 1500 |
| AGGTCCCCCC | ACTGCTGGCC | CTTCTACGGC | CACTACTGTG | CCTTTGAGTC | CGGTGGACGA | 1560 |
| TGCCTGCAAC | GTGAACATCT | TCGACGCCAT | CGCGGAGATT | GGGAACCAGC | TGTATTTGTT | 1620 |
| CAAGGATGGG | AAGTACTGGC | GATTCTCTGA | GGGCAGGGGG | AGCCGGCCGC | AGGGCCCCTT | 1680 |
| CCTTATCGCC | GACAAGTGGC | CCGCGCTGCC | CCGCAAGCTG | GACTCGGTCT | TTGAGGAGCC | 1740 |
| GCTCTCCAAG | AAGCTTTTCT | TCTTCTCTGG | GCGCCAGGTG | TGGGTGTACA | CAGGCGCGTC | 1800 |
| GGTGCTGGGC | CCGAGGCGTC | TGGACAAGCT | GGGCCTGGGA | GCCGACGTGG | CCCAGGTGAC | 1860 |
| CGGGGCCCTC | CGGAGTGGCA | GGGGGAAGAT | GCTGCTGTTC | AGCGGGCGGC | GCCTCTGGAG | 1920 |
| GTTCGACGTG | AAGGCGCAGA | TGGTGGATCC | CCGGAGCGCC | AGCGAGGTGG | ACCGGATGTT | 1980 |
| CCCCGGGGTG | CCTTTGGACA | CGCACGACGT | CTTCCAGTAC | CGAGAGAAAG | CCTATTTCTG | 2040 |
| CCAGGACCGC | TTCTACTGGC | GCGTGAGTTC | CCGGAGTGAG | TTGAACCAGG | TGGACCAAGT | 2100 |

```
GGGCTACGTG  ACCTATGACA  TCCTGCAGTG  CCCTGAGGAC  TAGGGCTCCC  GTCCTGCTTT    2160

GCAGTGCCAT  GTAAATCCCC  ACTGGGACCA  ACCCTGGGGA  AGGAGCCAGT  TTGCCGGATA    2220

CAAACTGGTA  TTCTGTTCTG  GAGGAAAGGG  AGGAGTGGAG  GTGGGCTGGG  CCCTCTCTTC    2280

TCACCTTTGT  TTTTGTTGG   AGTGTTTCTA  ATAAACTTGG  ATTCTCTAAC  CTTT          2334
```

(2) INFORMATION FOR SEQ ID NO:34:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:34:

```
Glu  Ala  Leu  Met  Tyr  Pro  Met  Tyr  Arg  Phe  Thr  Glu  Gly  Pro  Pro  Leu
1                   5                        10                       15
His  Lys
```